United States Patent [19]
Coelho et al.

[11] Patent Number: 5,964,095
[45] Date of Patent: Oct. 12, 1999

[54] METHOD AND APPARATUS FOR CRYOGENIC STORAGE OF THERMOLABILE PRODUCTS

[75] Inventors: Philip Henry Coelho, El Dorado Hills; Terry Wolf, Placerville, both of Calif.; Pablo Rubinstein, New Rochelle, N.Y.

[73] Assignee: ThermoGenesis Corp., Rancho Cordova, Calif.

[21] Appl. No.: 08/877,763

[22] Filed: Jun. 16, 1997

Related U.S. Application Data

[62] Division of application No. 08/393,558, Feb. 23, 1995, Pat. No. 5,638,686.

[51] Int. Cl.$^6$ .................................................... F25D 25/00
[52] U.S. Cl. ................................................. 62/62; 62/337
[58] Field of Search ........................... 62/62, 51.1, 336, 62/337

[56] References Cited

U.S. PATENT DOCUMENTS

| 3,662,565 | 5/1972 | Gram ............................ 62/345 |
| 4,090,374 | 5/1978 | Faust et al. . |
| 4,245,483 | 1/1981 | Murai ........................... 62/376 |
| 4,432,214 | 2/1984 | Richelli et al. . |
| 4,551,992 | 11/1985 | Sitte et al. .................... 62/51.1 |
| 4,757,692 | 7/1988 | McMonald .................... 62/51.1 |
| 4,768,356 | 9/1988 | Volker ........................ 62/51.1 |
| 4,920,763 | 5/1990 | Provest et al. . |
| 5,125,240 | 6/1992 | Knippscheer et al. ......... 62/266 |
| 5,176,202 | 1/1993 | Richard . |
| 5,233,844 | 8/1993 | Knippsheer et al. .......... 62/345 |

FOREIGN PATENT DOCUMENTS

| 0411224 | 2/1991 | European Pat. Off. ........ F25D 3/11 |
| 4507283 | 12/1992 | Japan ............................ F25D 3/11 |
| 6509782 | 11/1994 | Japan ............................ B65G 1/02 |
| 9102202 | 2/1991 | WIPO .......................... F25D 23/02 |
| 9102203 | 2/1991 | WIPO .......................... F25D 23/02 |
| 9109521 | 7/1991 | WIPO .......................... A01N 1/02 |
| 9216800 | 10/1992 | WIPO .......................... F25B 29/00 |
| 9303891 | 3/1993 | WIPO .......................... B25G 1/00 |

Primary Examiner—Ronald Capossela
Attorney, Agent, or Firm—Bernhard Kreten

[57] ABSTRACT

A device for cryoprotecting thermolabile products. A container (20) receives an annular rack (40) which is sealed by an enclosure (60). The enclosure (60) includes an outer stationary toroid (70) and a rotatable core (90). A robotic arm (160) is adapted to move and is supported by the core (90). The robotic arm (160) accesses an interior of the enclosure (60). An access portal (80) allows removal and placement of thermolabile products constrained by a holder (150). The robotic arm (160) accesses product and holder (150) and embarks upon controlled freezing of the product and its location in the rack (40) until subsequent retrieval. A computer controls the rate of freezing and stores in memory the location of all of the stored products. The robotic arm (160) reads the product in storage to assure the correct product is being accessed.

15 Claims, 13 Drawing Sheets

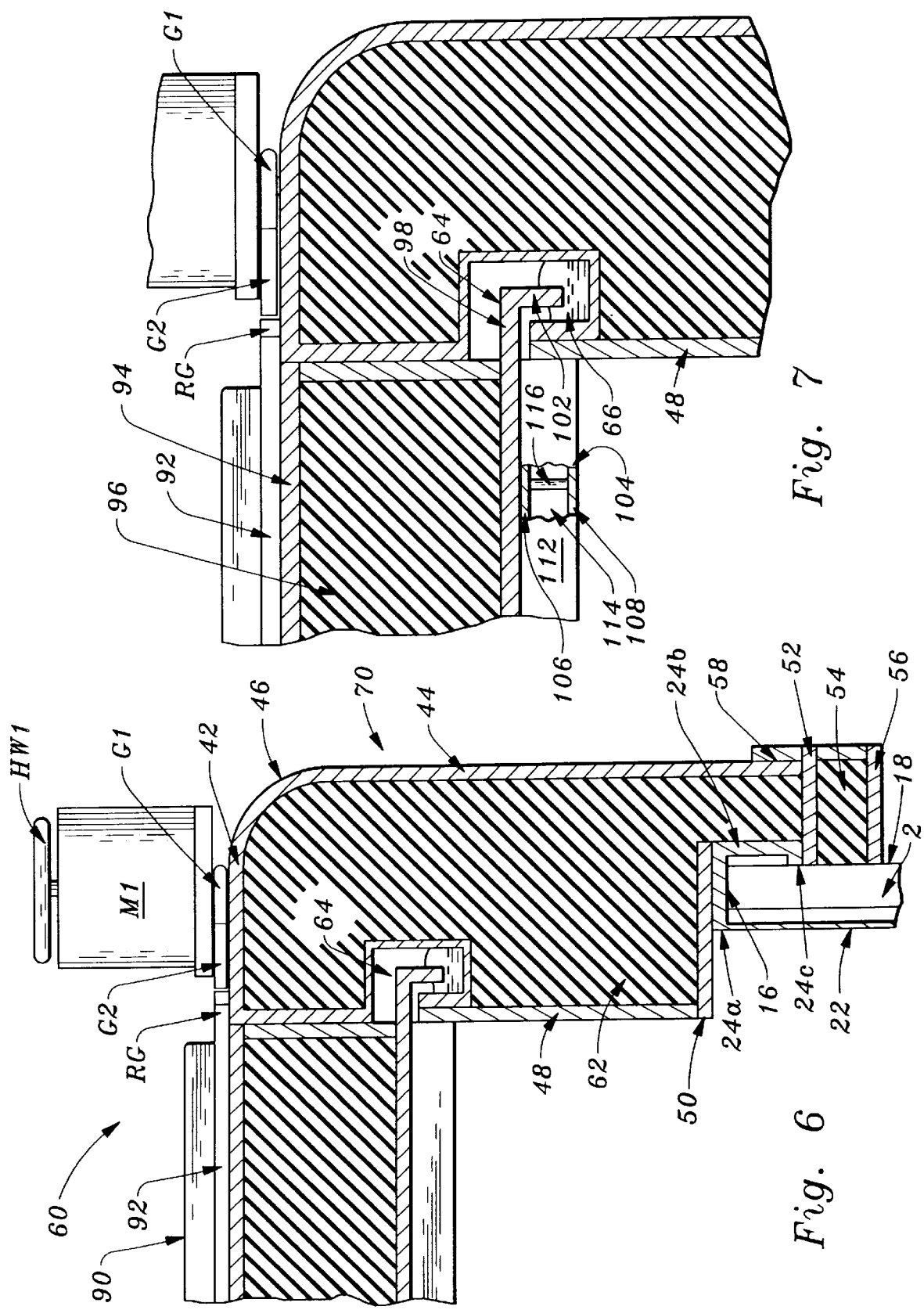

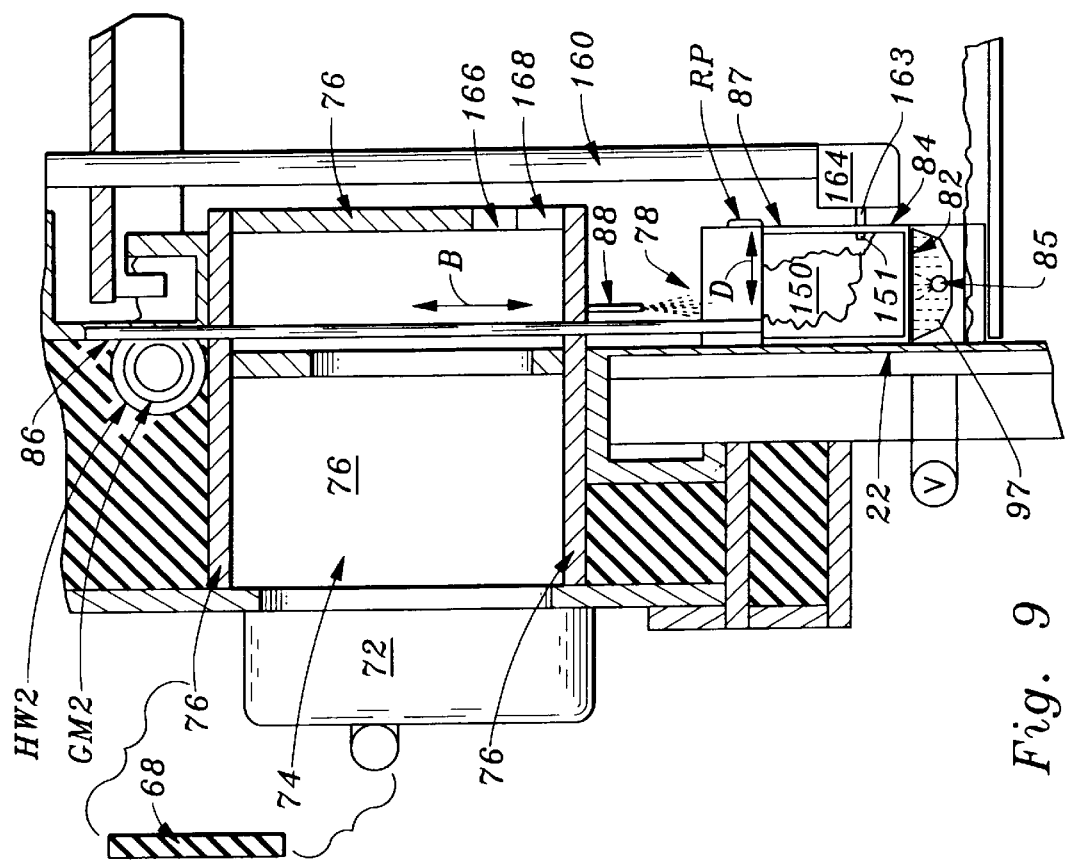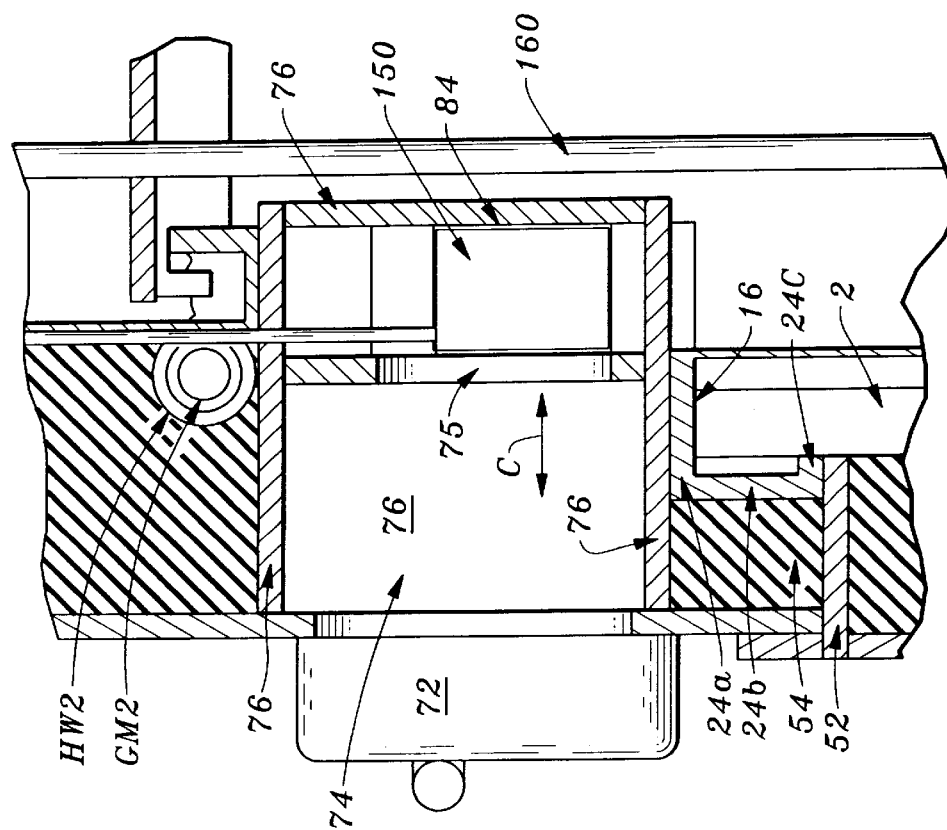

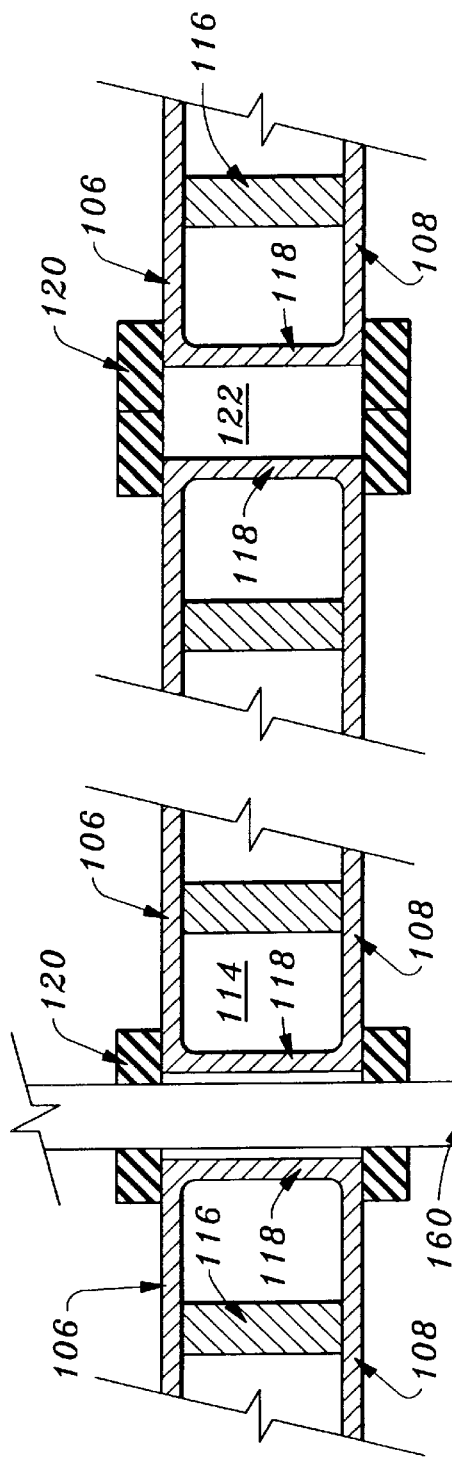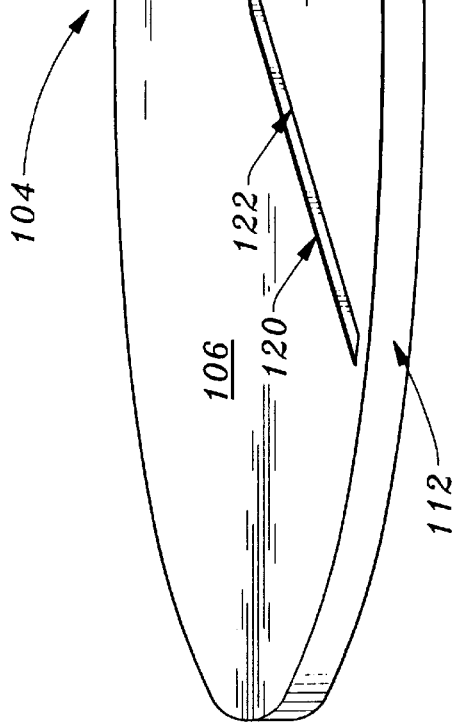

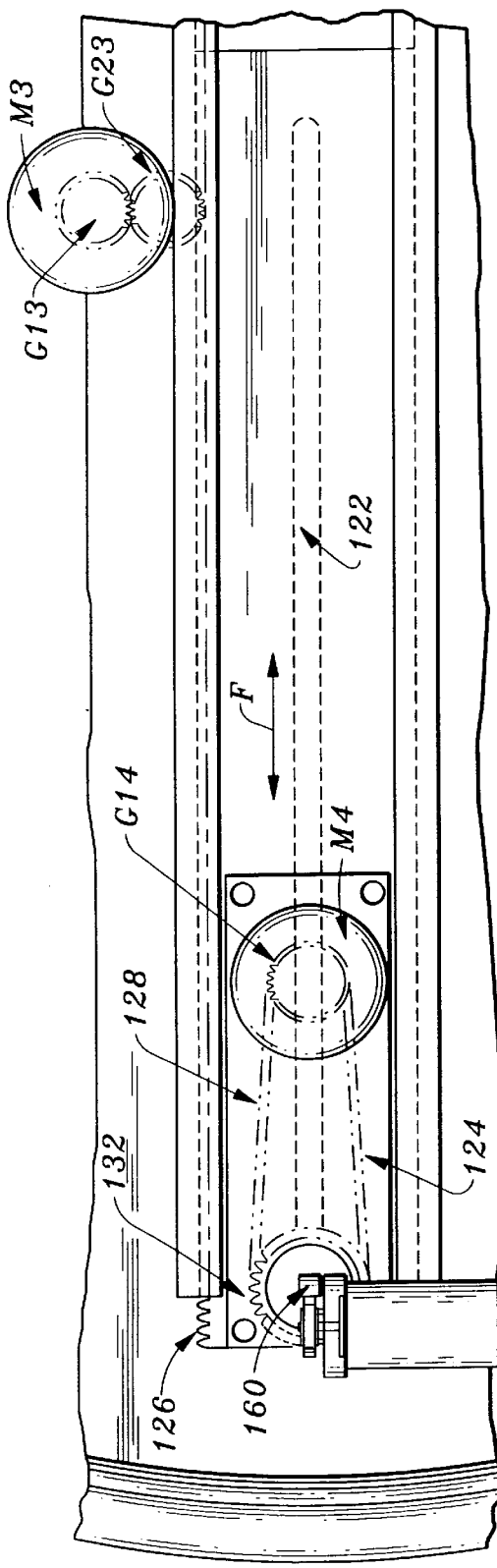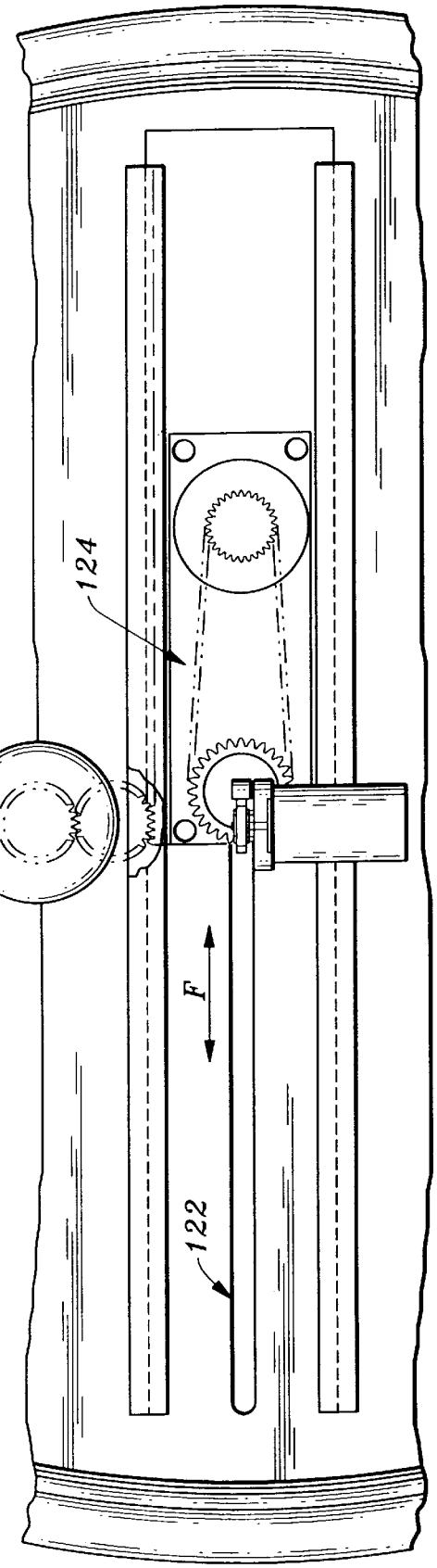
Fig. 13
Fig. 14

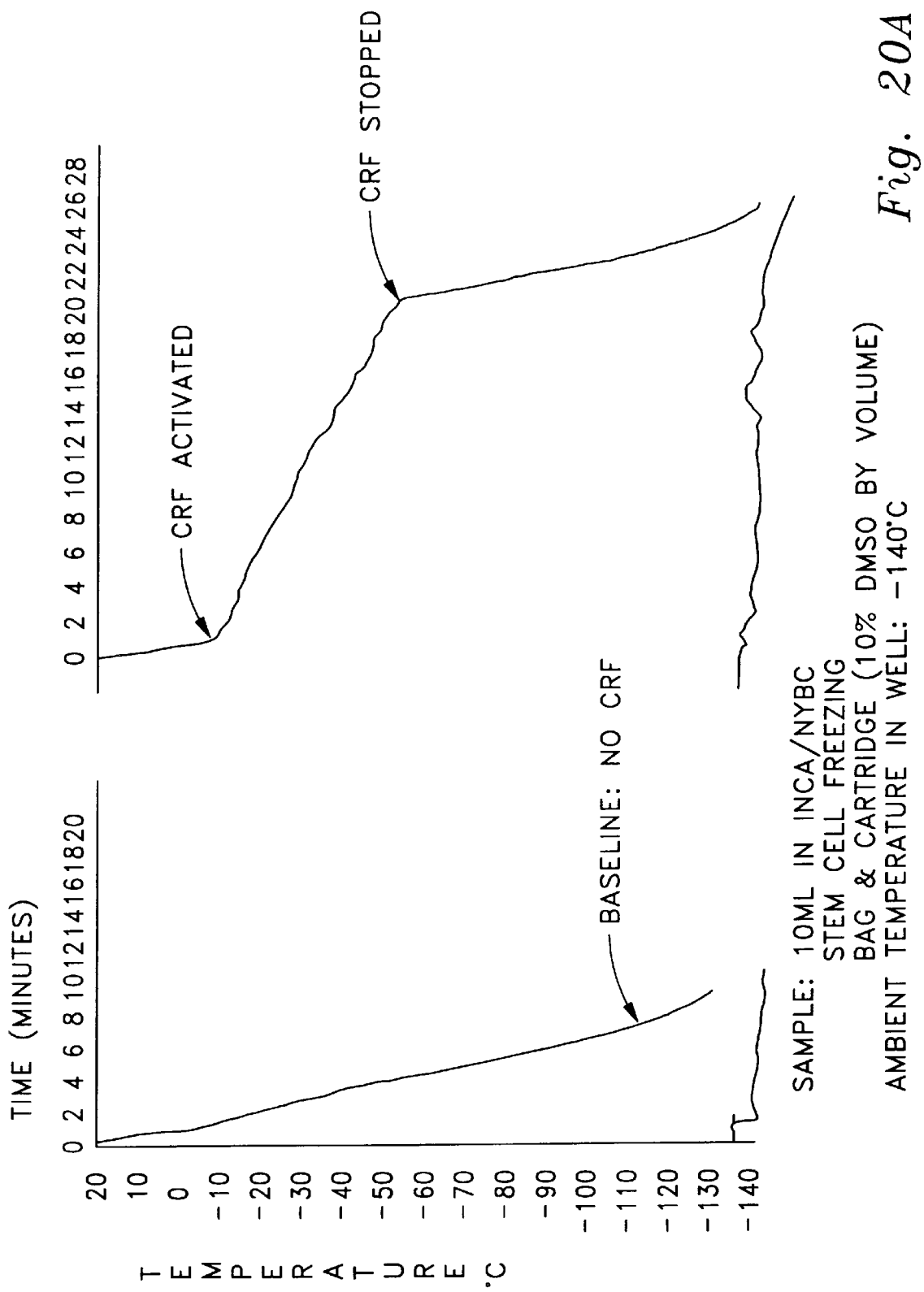

METHOD AND APPARATUS FOR CRYOGENIC STORAGE OF THERMOLABILE PRODUCTS

This application is a division of application Ser. No. 08/393,558, filed Feb. 23, 1995, now U.S. Pat. No. 5,638,686.

FIELD OF THE INVENTION

The following invention relates generally to a method and apparatus for storing a plurality of thermolabile products in a cold, preserving medium including storage addresses for each product in a cold storage container. Each product stored has a unique identity which correlates with both its source of origin and its location in the container. The device includes means for reading those identities. More specifically, this device especially enables tissue, DNA specimens, laboratory assays, certain blood products and especially white blood cells to be cryoprotected, decreased in temperature at a preprogrammed, controlled rate stored and subsequently accessed upon appropriate identification to be surrendered for subsequent use.

BACKGROUND OF THE INVENTION

The need to save thermolabile products, especially in the field of medicine and for its evidentiary value in law, continues to increase. Tissue sample, DNA specimens and laboratory assays are all examples of substances which, once studied, typed and matched are suitable candidates for subsequent storage should the need ever arise for further analysis. Products which can degrade as a function of time and temperature have little archival value unless properly preserved and maintained.

Significant advances in the state of the art in blood cell research, especially sequestering and preserving white blood cells and the discovery that these cells can be used between unrelated donors and recipients, has created a need for a reliable freezing and storage device for the blood products, especially blood cells to maintain their quality prior to utilization. Although there is no longer an absolute requirement that donors and recipients be related, matching characteristics of the donor and the recipient presently optimizes the likelihood of acceptance by the recipient rather than rejection. Based on a multiplicity of factors, it is estimated that optimally matching a donor to a recipient may require selecting from an aggregation of donor specimens numbering in the thousands or even hundreds of thousands.

The problem associated with storing large numbers of donor's products is that they are thermolabile and therefore can degrade as a function of time when they are not frozen at a controlled rate and then maintained in an extremely low-temperature, controlled environment. Equally as important, once the products are stored in the appropriate low temperature environment, it is still highly desirable that the product remain stable and undisturbed at that temperature until the product is to be used. This assures the highest quality.

These foregoing considerations provide considerable engineering problems, especially should the products be stored at temperatures where nitrogen is the cold storage liquid, because mechanisms working in such an operating environment would have to be durable at −190° C. At such low temperatures, tasks which are relatively simple at room temperature, e.g. storing, selecting and removing products provide difficulties. Mechanical implements can be prone to failure at extremely low temperatures. Should there be a mechanical failure without adequate accommodation for some type of system redundancy, there can be dire consequences both as to timely treatment and as to maintaining product quality because of failure to access or maintain the product at a constant temperature.

The following patents reflect the state of the art of which applicant is aware insofar as these patents appear germane to the process at hand. However, it is stipulated that none of these patents singly nor when considered in any conceivable combination teach the nexus of the instant invention as set forth hereinabove and as particularly claimed.

| PATENT NO. | ISSUE DATE | INVENTOR |
|---|---|---|
| U.S. PATENT DOCUMENTS | | |
| 5,125,240 | June 30, 1992 | Knippscheer, et al. |
| 5,233,844 | August 10, 1993 | Richard |
| FOREIGN PATENT DOCUMENTS | | |
| EP0 411 224 A2 | February 2, 1991 | Knippscheer, et al. |
| WO91/02202 | February 21, 1991 | Richard |
| WO91/02203 | February 21, 1991 | Knippscheer, et al. |
| WO91/09521 | July 11, 1991 | Richard |
| WO92/16800 | October 1, 1992 | Knippscheer, et al. |
| WO93/03891 | March 4, 1993 | Knippscheer, et al. |
| JP4-507,283 | December 17, 1992 | Knippscheer, et al. |
| JP6-509,782 | November 2, 1994 | Knippscheer, et al. |

The several patents to Knippscheer, et al. teach the use of a storage device for cryoprotecting thermolabile products including means for selectively extracting certain products upon demand. All these prior art teachings can be collectively characterized as requiring complex mechanical mechanisms whose moving components are required to perform reliably at a temperature in which liquid nitrogen is intended to be present. Because relative motion of mechanical implements is described, maintenance, repair and lubrication of the implements and reliability at such low temperatures is a grave concern. The instant invention is distinguished over the Knippscheer, et al. patents, inter alia, in that no moving components have drive mechanisms that contact or operate directly in the liquid nitrogen.

SUMMARY OF THE INVENTION

The instant invention solves the problems which plague the prior art in a multiplicity of ways. The instant invention provides a sealed container having a series of annular racks concentrically disposed therewithin. Each of the racks is maintained in a fixed position with respect to peripheral walls of the container. Liquid nitrogen covers the racks. Each annular rack is separated one from the other by an annular passageway. The annular passageways provide access to the racks and therefore to thermolabile products which are stored in the racks.

Head space is provided between a surface of the liquid nitrogen and an uppermost extremity of the container. The head space is provided with nitrogen gas to continue maintaining a low temperature. An access portal is also located above the liquid level to communicate with the ambient conditions.

The upper extremity of the container is closed. The enclosure may include the following structure. First, the overlying enclosure is sealed to form a gas cap. Specifically, a first platen overlies the topmost extremity of the container. This first platen prevents the nitrogen gas from escaping and provides a thermal barrier. An insulating space also exists above the platen. The enclosure circumscribes and overlies both a topmost portion of the container and the entire platen. Collectively, the enclosure and platen provide barriers to prevent both heat and ambient moisture contained in air from migrating into the container.

Second, the enclosure provides a support structure for a robotic arm drive mechanism. A robotic arm connects to the drive mechanism and extends through the platen to access the racks and the thermolabile products contained in the racks via the annular passageways. The robotic arm can move to selected sites in the racks and transfer thermolabile products from the racks to the access portal and back. The robotic arm also includes an indexing mechanism which initializes and orients the arm with respect to its position vis-a-vis a reference, which perhaps is fixed in the container. The robotic arm includes means for reading indicia either contained on an exposed surface of the thermolabile product, or on a holder which encapsulates the thermolabile product. The robotic arm transmits that information from the thermolabile product or holder to a remote reading and memory site. The desirability of orienting and indexing of the robotic arm, coupled with its remote reading and memory capability increases the likelihood that only the desired thermolabile product is extracted from the container. In the case of insertion of the thermolabile product into the container, the storage address of the thermolabile product will be known.

OBJECTS OF THE INVENTION

Accordingly, it is a primary object of the present invention to provide a new, novel and useful method and apparatus for cryogenic storage of thermolabile products.

A further object of the present invention is to provide a device as characterized above which is extremely durable in construction, safe to use, and lends itself to mass production.

A further object of the present invention is to provide a device as characterized above in which the extreme low temperature operating environment is below all moving machinery associated therewith for added reliability and freedom from maintenance problems.

A further object of the present invention is to provide a device as characterized above in which thermolabile products that are stored at cryogenic temperatures can be delegated to a specific address in the storage device and remain there until subsequently needed.

A further object of the present invention is to provide a device as characterized above in which each thermolabile product contained in storage is first scanned for verification purposes to increase the likelihood that only the correct product is being removed from storage so as to prevent unwanted temperature excursions, particularly temperature elevations, of the product.

A further object of the present invention is to provide a device as characterized above in which each thermolabile product contained in storage is first scanned prior to removal to increase the likelihood that only the correct product is being removed from storage so as to minimize any physical disturbance of the product until such removal is desired.

Viewed from a first vantage point it is an object of the present invention to provide a device for storing and accessing thermolabile products, comprising, in combination: a container, liquid in the container, means for maintaining the liquid at a depressed temperature, an annular storage rack disposed in the liquid in the container and including plural compartments dimensioned such that one thermolabile product can be received in any one of the plural compartments, an access portal located above the liquid and communicating outside the device, and means for transporting the thermolabile products to and from the compartments and the access portal.

Viewed from a second vantage point it is an object of the present invention to provide a method for storing and retrieving thermolabile products, the steps including orienting the thermolabile product adjacent the container, allowing the thermolabile product to enter the container, grasping the thermolabile product with a robotic arm, allowing the thermolabile product to decrease in temperature at a controlled rate, storing the thermolabile product in a specific site, memorizing the location of the specific site and subsequently retrieving the thermolabile product by recalling the specific site of the thermolabile product, directing the robotic arm to the memorized site of the thermolabile product, verifying that the desired thermolabile product has indeed been identified at the memorized site, attaching the robotic arm to the thermolabile product, and delivering the thermolabile product to an exterior of the container.

Viewed from a third vantage point it is an object of the present invention to provide a holder for a thermolabile product which allows the thermolabile product to be contacted by a robotic arm, comprising, in combination: means for attaching said holder to said thermolabile product and means for attaching said thermolabile product to said robotic arm through said holder.

Viewed from a fourth vantage point it is an object of the present invention to provide a holder to allow a thermolabile product to be accessed by a robotic arm, comprising, in combination: said holder having indicia associated therewith correlative of indicia on said thermolabile product and means on said robotic arm for reading said indicia.

Viewed from a fifth vantage point it is an object of the present invention to provide a cryogenic device comprising a robotic arm adapted to move between a first position and a second position, said first position accessing thermolabile product which is stored at depressed temperatures, said second position adapted to allow said thermolabile products access to ambient conditions, and remote reading means operatively coupled to said robotic arm for assuring a correct thermolabile product has been selected by said robotic arm.

Viewed from a sixth vantage point it is an object of the present invention to provide a unitary cryogenic device which both freezes a thermolabile product at a controlled rate and stores the frozen product.

Viewed from a seventh vantage point it is an object of the present invention to provide a thermolabile product in a black box holder and expose the holder and product through a controlled rate temperature excursion.

These and other objects will be made manifest when considering the following detailed specification when taken in conjunction with the appended drawing figures.

BRIEF DESCRIPTION OF THE DRAWINGS

FIG. 6 is a sectional view of upper right-hand toroid of FIG. 1.

FIG. 7 is greater detail of that which is shown in FIG. 6.

FIG. 8 is a sectional view of an access portal shown in FIG. 1 with an elevator in an "up" position.

FIG. 9 is a sectional view of an access portal shown in FIG. 1 with an elevator in an "down" position.

FIG. 10 is a sectional view of a distended seal on a platen.

FIG. 11 is a sectional view of a seal on the platen.

FIG. 12 is perspective view of the platen.

FIG. 13 is a top view of the device.

FIG. 14 is a top view of the device.

FIG. 20A is one algorithm showing the benefit of controlled rate freezing as a function of temperature.

DESCRIPTION OF PREFERRED EMBODIMENTS

Figure 1:
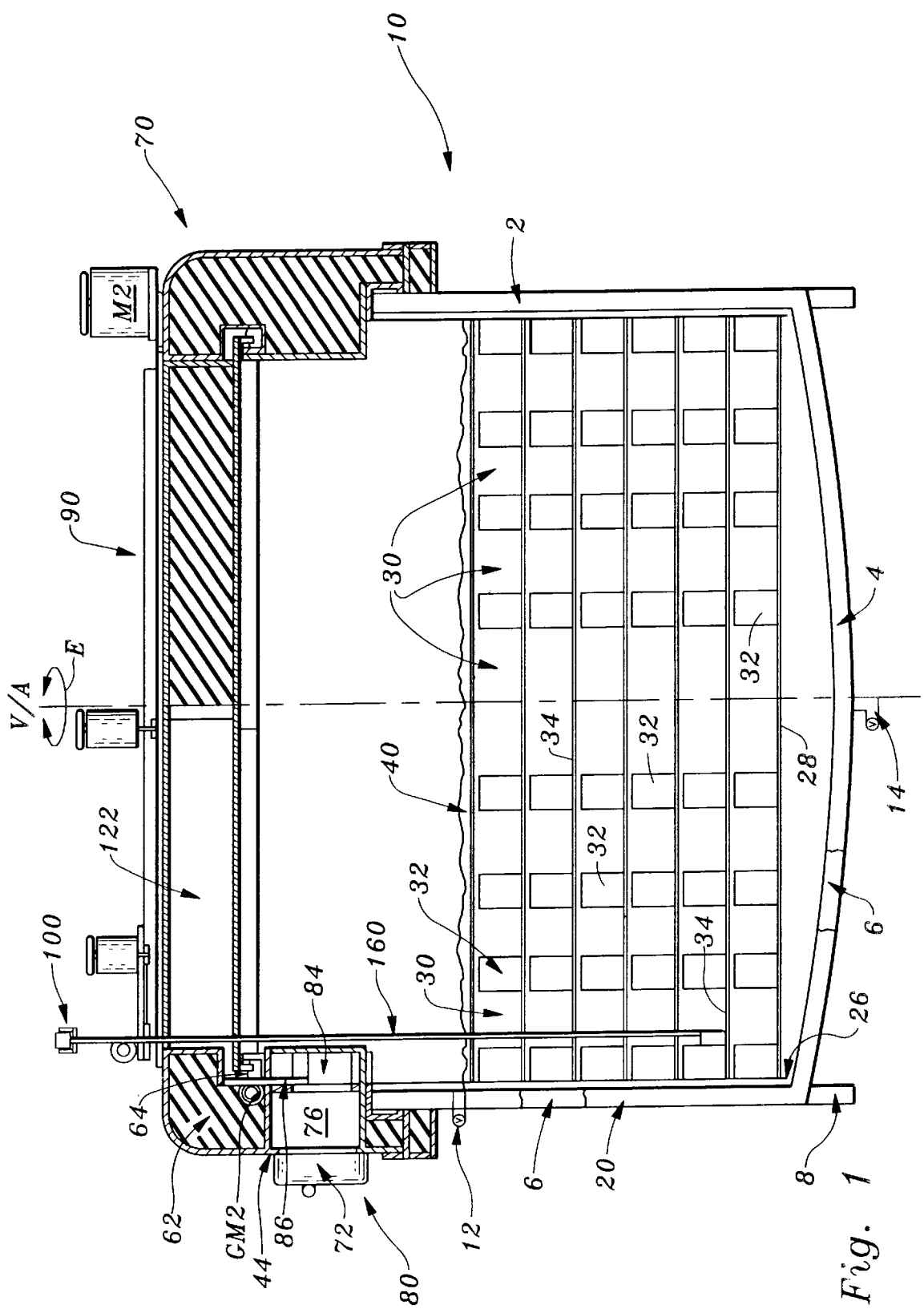
FIG. 1 is sectional view along a vertical plane at a diameter of the device.

Referring to the drawing, wherein like numerals denote like parts throughout the various figures, reference numeral 10 is directed to the apparatus for the cryogenic establishment and storage of thermolabile products.

Figure 2:
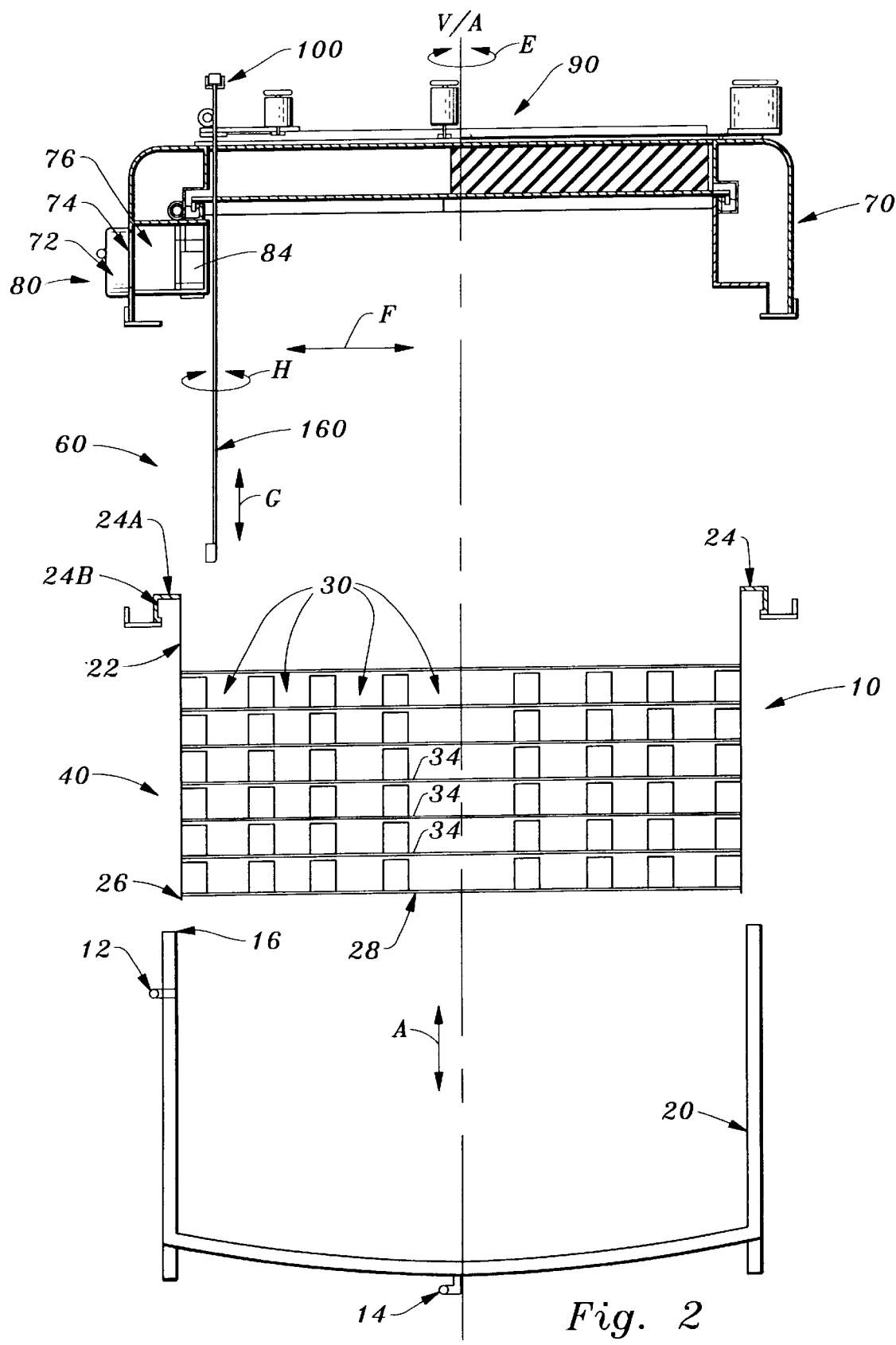
FIG. 2 is an exploded parts view of that which is shown in FIG. 1.

In essence, and with respect to FIGS. 1 and 2 in particular, the device 10 includes three major assemblies: a container 20 adapted to receive liquid nitrogen therewithin, an annular rack 40 dimensioned to slideably and nestably fit within an interior of the container 20, and an overlying enclosure 60 which seals the container and the annular rack from ambient conditions. At least one access portal 80 is provided, preferably located within the enclosure 60 to allow thermolabile product (to be described in detail hereinafter) to be admitted and removed from the device 10. The access portal 80 communicates with a transporting means 100 that includes a robotic arm 160 and drive mechanism for moving the thermolabile products to and from the access portal 80 and the annular storage rack 40.

More particularly, and with particular reference to FIGS. 1 and 2, the details of the container 20 can be explained. In essence, this container is preferably a commercially available container conventionally used to store liquid nitrogen and is commonly referred to as a "pressure" vessel. Because of the extremely low temperature (e.g. −190° C.), the container 20 is formed with a peripheral side wall 2 integrally formed with a base 4 having an arcuate bottom contour where a convex side of the arcuate contour faces downwardly. An interior sectional view of the pressure vessel container 20 shows that an interior hollow 6 is provided which is maintained at a near vacuum as is commercially practicable. This vacuum discourages thermal invasion. The hollow 6 may also be filled with foam. Legs 8 keep the container 20 stable above the ground to preclude thermal transfer. Thus, the container 20 is an open topped blind bore having a concave bottom interior wall adapted to receive liquid nitrogen therewithin. As is common with these commercially available pressure vessel containers, plumbing in the form of an inlet 12 controlled by valve V and an outlet 14 also controlled by a valve V allow for the respective adding, replenishing or removing of the liquid nitrogen as is needed.

Referring to FIGS. 1 through 5, details of the annular rack 40 can be put into perspective. As shown, the annular rack 40 has an exterior dimension complemental with the interior bore of the container 20. Thus, the rack 40 lends itself to slideable insertion within the blind bore of the container 20 and to rest therewithin. Double ended arrow A of FIG. 2 reflects the direction of removable insertion and extraction with respect to the container 20.

The rack 40 includes a peripheral wall 22 having at its topmost extremity a downwardly open substantially "U"-shaped rack support 24. The U-shaped rack support 24 faces outwardly and is oriented to overlie a topmost edge 16 of the container 20. The rack support 24 includes a bight portion 24a and a downwardly extending leg 24b adapted to straddle the exterior of the container 20 in conjunction with the peripheral wall 22.

Figure 3:
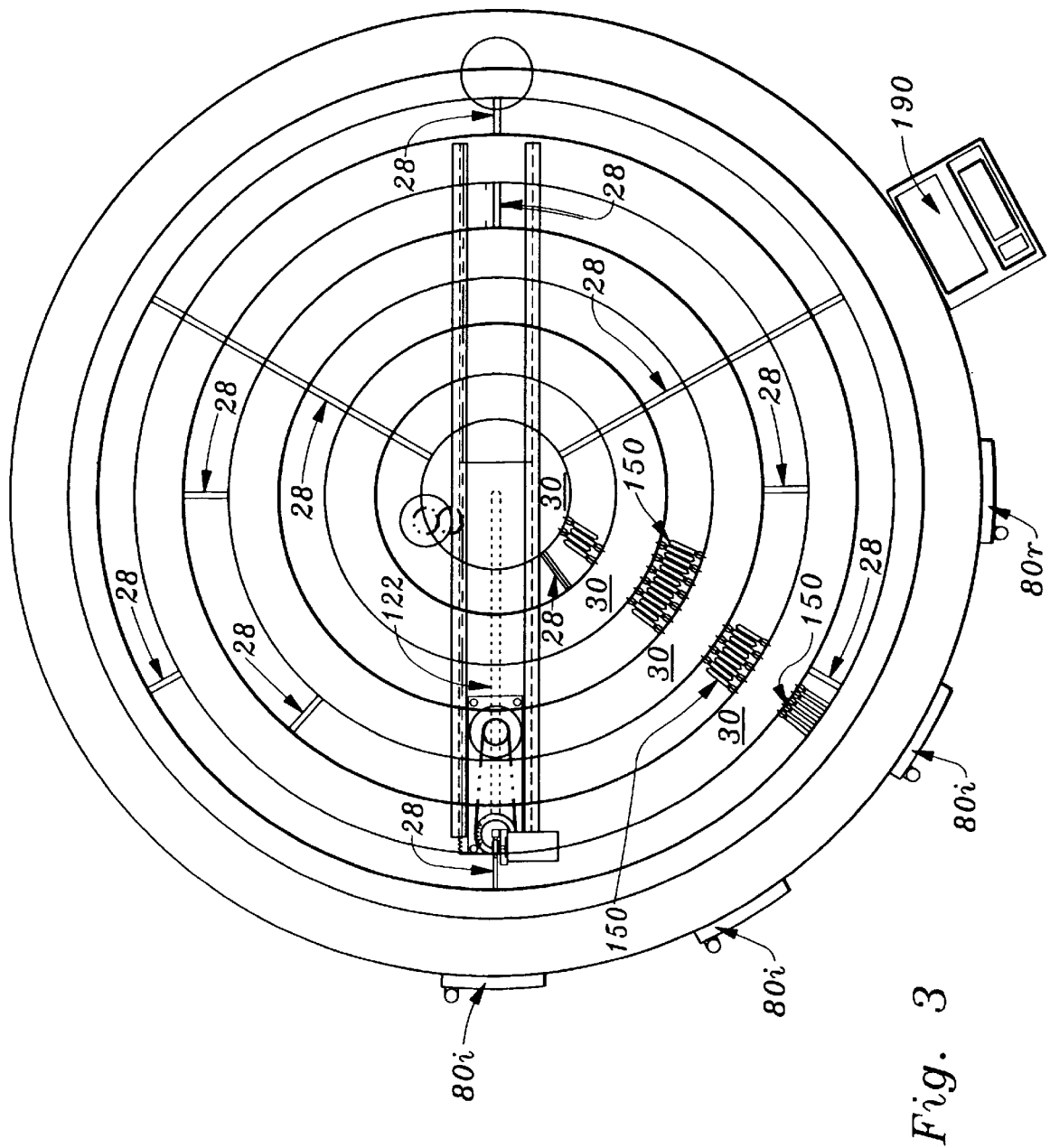
FIG. 3 is a top view with certain interior portions exposed.

In addition, the rack 40 may be supported by means of plural feet 26 projecting downwardly from the peripheral wall 22 so that rack 40 rests upon the upper concave surface of the bottom 4 of the container 20. The rack 40 includes a floor 28 which is substantially circular and may be formed from a plate or a plurality of ribs which form a network extending to the peripheral wall 22. For example, FIG. 3 shows a plurality of radially extending ribs 28 as one floor embodiment connecting the peripheral wall 22 and providing support for a series of concentrically disposed arrays of compartments 32. The arrays of annular compartments are separated from one another towards the geometrical center of the rack 40 by means of annular passageways 30. The centralmost passageway is a cylinder. Thus, given the dimensions of one commercial container 20, a series of four concentrically disposed arrays of compartments are shown and provided having the configuration.

Figure 5:
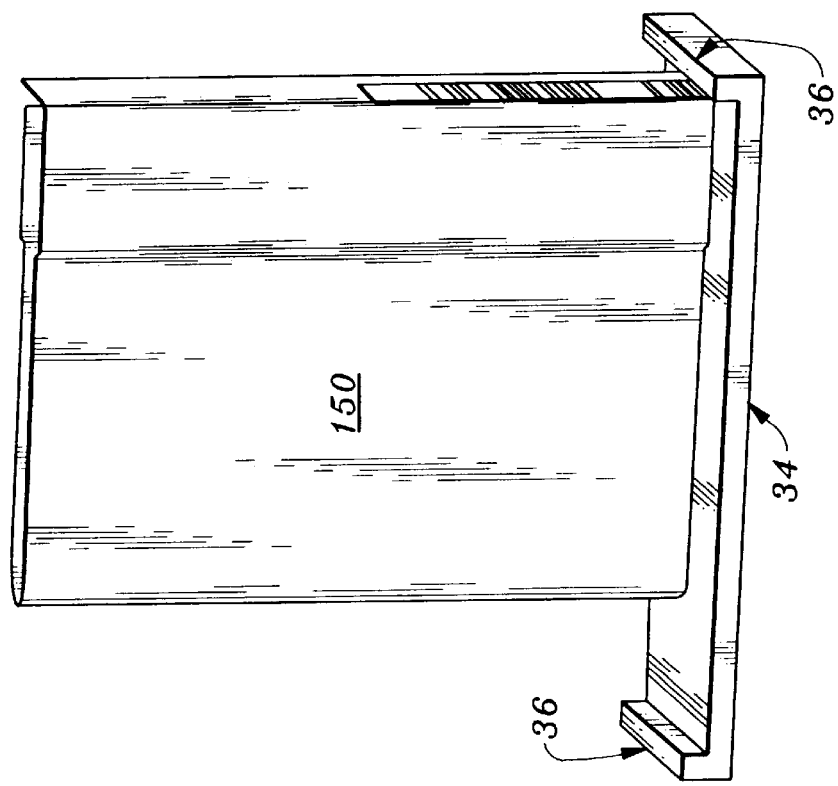
FIG. 5 is a side perspective view of a portion of the FIG. 4 shelf with the compartment removed.
Figure 4:
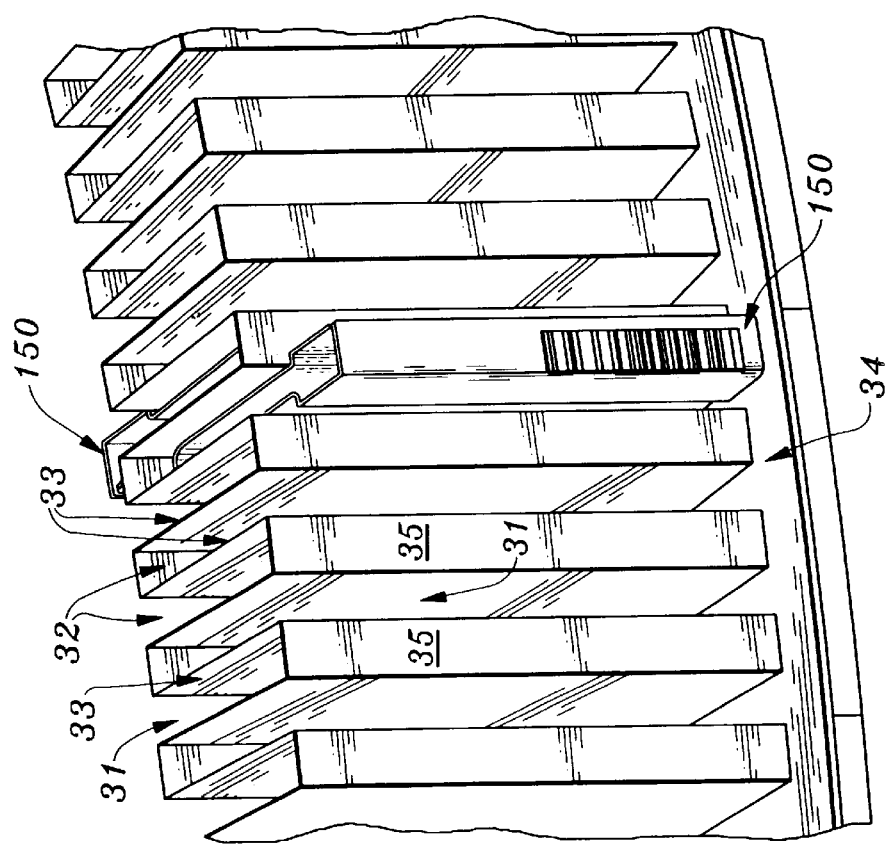
FIG. 4 is a perspective view of one of the interior storage shelves showing access to both sides thereof.

As shown in FIGS. 4 and 5, the plurality of compartments 32 have a bottom shelf 34 with a peripheral lip 36 at both inboard and outboard arcuate edges thereof. The compartments 32 may be provided with partitions 33 that allow holders 150 to be held in fixed position within the storage rack 40. The compartments 32 are formed from one continuous sheet contoured as a serpentine wall with partitions 33 connected by ends 35. Access openings 31 allow holders 150 to be alternately facing adjacent passageways 30.

As shown in FIG. 3, for example, the outermost shelf (i.e. that which is immediately adjacent the peripheral wall 22) stores the holders 150 such that the outboardmost annular passageway 30 faces these holders 150. The successive inwardly directed three sets of shelves 34, however, support compartments 32 that open on both an interior arcuate edge of the shelf 34 and an exterior arcuate edge of the shelf as shown in FIGS. 4 and 5. This allows the holders 150 to be interleaved with respect to adjacent holders 150 thereby increasing the density of the number of holders capable of being inserted. The interleaving benefits from the fact that the holders 150 have a wedge-shaped contour which accommodates the wedge-shaped contour of each compartment 32. Only the shelves 34 nearest wall 2 do not benefit from this interleaving feature. Attention is now directed to FIGS. 1, 2 and 6 through 10. These drawings reflect certain other details with respect to the enclosure 60 which overlies the container 20 and associated storage rack 40. As briefly mentioned, supra, the enclosure 60 serves as a support for both the access portal 80, the transporting means 100 and for the robotic arm 160. One hallmark of the enclosure is that it can be removed as a monolith as suggested in FIG. 2 so that, should the container 20 leak or require replacement for some other reason, the rack 40 can be moved as one entity and all of the thermolabile product contained therewithin can be expeditiously moved for subsequent storage elsewhere. The enclosure 60 includes a stationary toroid 70 which does not move relative to the container 20 during normal use and operation. The toroid 70 supports the access portal 80. In addition, the enclosure 60 includes a central core 90 which is surrounded by the toroid 70. The core 90 defines a portion of the transporting means 100 for the robotics to be described.

More particularly, the enclosure's stationary toroid 70, shown at its right-hand portion in FIG. 6, provides a support for a motor M1 which is used to drive the core 90 about a vertical axis VA which is located at the geometric center of the apparatus 10 and shown in FIGS. 1 and 2. The toroid 70 also includes an effective seal to preclude the effect of thermal migration. For example, the toroid 70 contacts an outer surface 18 of side wall 2, rests upon the bight portion 24a of the downwardly open U-shaped rack support 24, and frictionally engages the outboard vertical leg 24b of the bight portion. Notice in FIG. 6 that the terminal extremity of the vertical leg 24b of the U-shaped rack support includes an inwardly directed contacting lip 24c made of insulated material to serve as a further barrier against thermal migration.

The motor M1 is supported atop a top skin 42 of the toroid 70. The top skin 42 communicates with a vertically disposed outside skin 44. An area of transition, defined by a radiused edge 46 communicates between the top skin 42 and the outside skin 44. Vertical inside skin 48 is parallel to and spaced from the vertical outside skin 44. In addition, a horizontal bottom skin 50 is disposed at a lowermost extremity of the vertical inside skin 48. The horizontal bottom skin 50 is adapted to lie atop, seal and distribute weight onto the U-shaped rack support 24 discussed hereinabove. In addition, the vertical outside skin 44 extends to the same horizontal plane of the lip 24c of the U-shaped rack support.

Because of the extremely low temperature differential between the operating temperatures of the interior of the container 20 and the exterior, a further seal 52 is horizontally disposed and located below both the lip 24c and a free end of the vertical outside skin 44. This toroidal seal 52 can be removably fastened by means of a toroidal tang 58 integrally formed therewith. Tang 58 is vertically oriented and adapted to be removably fastened to an outside surface of the vertical outside skin 44. In this way, the enclosure 60 can be removed independently from the rack 40 if desired by removal of the tang 58 and seal 52. With the horizontally disposed toroidal seal 52 in place, however, the enclosure 60 and rack 40 can be removed as one element. The toroidal seal 52 is enhanced with respect to its sealing ability by means of insulation 54 located directly below the seal 52 and held in place by means of a toroidal pad 56 located on a bottom surface of the insulation 54. The toroidal tang 58 can extend all of the way down to the toroidal pad 56 for added support. Means for attaching the tang 58 to the vertical outside skin 44 can take the form of removable fasteners as should now be evident. The toroidal pad 56 provides sufficient support so that should the enclosure 60 be removed separately from the rack 40, the pad 56 can be load bearing.

An interior of the space defined by the outer contour of the inside skin 48, bottom skin 50, seal 52, outside skin 44 and top skin 42 includes insulation 62 to add to the thermal efficiency. As mentioned, the core 90 is constructed to move with respect to the stationary toroid 70. Because of the relative motion, an opportunity exists for thermal migration between these two components. Thus, a well 64 is provided and detailed in FIG. 7. As shown, the well 64 is located on a surface of the vertical inside skin 48 and is contoured as a recess. Well 64 includes an area to capture an insultative thermal lubricant such as silicon oil 66. One of the moving components (platen 104) of the core indirectly supports a seal 102 (to be described hereinafter) which resides within the well 64 and is ensconced by the silicon oil 66 for both lubrication and sealing benefits. Clearance above the well 64 is provided to allow the removable placement of the rotatable core 90 with respect to the well 64. The toroid 70 can be formed from sections in order to facilitate this fabrication and removal.

Referring to FIGS. 1, 2, 8 and 9, features with respect to the access portal 80 can now be explored. In its essence, the portal 80 allows the thermolabile product and its associated holder 150 access to the interior of the device 10. The access portal 80 preferably includes a door 72 which communicates with a vestibule 74 which, in turn, passes through the toroid 70 of the enclosure 60. The vestibule 74 is an opening formed within the toroid, penetrating into the insulation 62. The vestibule 74 is circumscribed on four walls (exclusive of the door 72) by means of a skin 76. Thus, the vestibule 74 has two side skins, a bottom skin and a top skin extending in from the door 72. If it appears that thermal migration within the vestibule is a problem, a plug 68 may be frictionally disposed within the vestibule 74 when the portal 80 is not in use.

The vestibule 74 communicates with an elevator 75 located at an end of the vestibule 74 opposite the door 72. The elevator has an elevator top wall 78 (FIG. 9), an elevator bottom wall 82 and a pair of opposed side walls 84. Accordingly, access is provided between the elevator 75 and the vestibule 74 (FIG. 8) so that a blood product and its associated holder 150 can gain access to the elevator by moving the product and holder 150 along double ended arrow C. Note that an end wall 76, opposite the door 72, prevents the blood product and holder 150 from being pushed through the elevator 75 when it is in the up position. FIG. 8 shows the elevator in an "up" position. FIG. 9 shows the elevator in a "down" position. The blood product and holder 150 is exposed to an interior of the device 10 as symbolically indicated with double arrow D.

Figure 16:
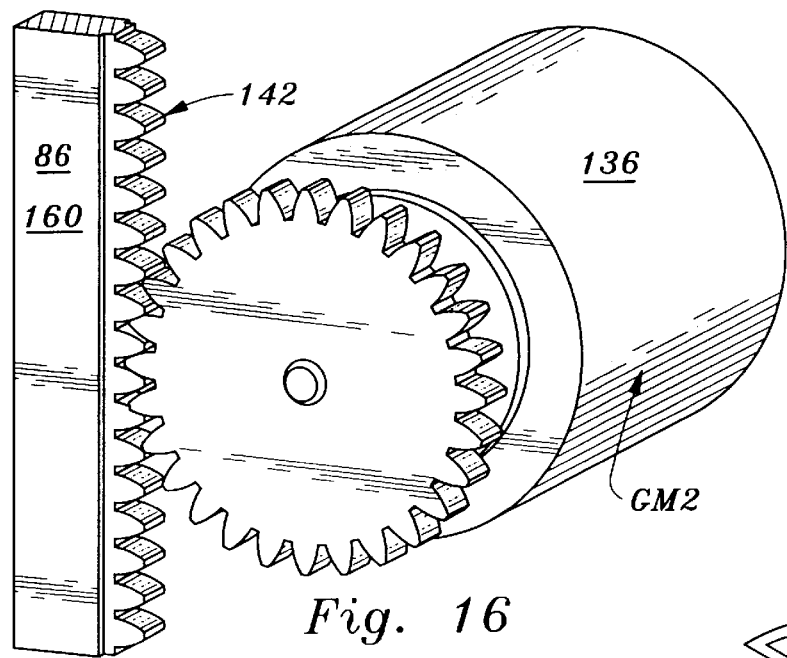
FIG. 16 is a perspective view of a motor drive used in the device.

The elevator 75 is adapted to move along the direction of the double ended arrow B by manipulation of a drive screw 86. FIGS. 8 and 9 show extreme positions of the elevator caused by manipulation of the drive screw 86. FIG. 1 graphically depicts a drive mechanism for the drive screw 86. In this version, a motor having a gear, GM2, directly connects to the drive screw 86 causing translation thereof similar to a rack and pinion assembly. FIG. 16 provides further detail. The operative coupling of the drive screw 86 to the top wall 78 of the elevator 75 facilitates motion of the elevator 75 as set forth. In the alternative a hand wheel HW2 can be used to manually drive the drive screw 86.

With respect to FIGS. 7, 10, 11 and 12, details of the core 90 can now be explored. In essence, the core 90 moves about the vertical axis VA and arrow E shown in FIG. 1. In order to afford the core 90 this motion, a driven turntable 92 (FIG. 7) is located on a top of the core 90. The turntable 92 includes an overlap portion which communicates with the motor M1 of FIG. 6. Specifically, the turntable includes a ring gear RG which laps over and extends on top of the toroid's top skin 42. Ring gear RG meshes with gear G2 of motor M1. Gear G1 is directly driven by the motor M1, whereby rotation of the motor M1 causes concomitant rotation of gear G1, G2 and therefore ring gear RG and the turntable 92. Motor M1 may be turned by a hand wheel HW1.

The turntable 92 (FIG. 7) is connected to an insulated body including a shell 94 of substantially hollow disc-shape construction within which insulation 96 is disposed. A bottom wall of the insulated shell 94 includes a peripherally extending projection 98. The projection 98 includes a downwardly depending flange seal 102 (FIG. 7) residing within the well 64 mentioned supra. The downwardly extending flange seal 102 is ensconced in the silicon oil 66 to retard thermal throughpassage and provide lubrication for a bearing surface.

In addition, the bottom surface of the shell 94 is held in communication with a platen 104 which has an upper plate 106 adhered to the bottom surface of the shell 94. Platen 104 includes a lower plate 108. The upper plate 106 is spaced from the lower plate 108 of the platen by means of a cylindrical plate side wall 112. An interior 114 of the platen is provided with a void which may include a vacuum because of its thermal properties. Spacers 116 are interposed between the upper plate 106 and lower plate 108 to provide strength. FIGS. 10 and 11 reflect further details of the platen 104. A seal 120 is located on slit walls 118 of the platen for purposes to be assigned. See also FIG. 12 which is a perspective view of the platen 104.

In essence, the ring gear RG in combination with the turntable 92 and motor M1 define the first of four transporting means 100 which allows a robotic arm 160 to access the interior of the device 10 to place and remove product therewithin. A slit 122 is provided in the platen 104 and passes through the shell 94, its insulation 96 and the turntable 92. This allows the robotic arm 160 to communicate with the interior of the device 10 and selectively access the elevator 75, holders 150, products associated therewith and the storage rack 40.

There is preferably one slit 122 passing through the core 90. Nonetheless, the robotic arm 160 accesses all of the annular passageways 30 within the device 10. Thus, it is necessary that the core 90 rotate about its vertical axis VA (i.e. about the double ended arrows E of FIG. 1). This is caused by the ring gear RG operatively coupled to the turntable 92 and motor M1. In addition, the robotic arm 160 moves radially (i.e. in the direction of the double ended arrow F of FIG. 2). Arm 160 also moves vertically (about the double ended arrows G of FIG. 2). Arm 160 also moves about the long axis of the robotic arm 160 (about the double ended arrows H) To afford radial motion along the direction of the double ended arrow F, the slit 122 (FIG. 14) passes entirely through the core 90. That is, the slit 122 passes through the turntable 92, the shell 94, the insulation 96, and the platen 104. As shown in FIG. 12, the slit 122 does not extend to the outermost extremity of the platen 104 or the shell 94 or insulation 96. The robotic arm 160 moves within the slit 122. In order to minimize the thermal losses, and as shown in FIGS. 10 and 11, the slit 122 is protected by a plurality of seals 120, two of which may be located above and below the platen 104. The seals 120 are located on respective sides of the slit 122, above slit walls 118 of the platen 104 and are supported on the platen's upper plate 106 and lower plate 108. FIG. 10 shows the seal 120 distended while the robotic arm 160 is contacting that part of the seal 120. FIG. 11 shows that the seal 120 is characterized as having sufficient elasticity and memory to return to an undeformed state once the robotic arm 160 has been advanced along the length of the slit 122. Thus, the robotic arm 160 is protected around its outer periphery at the platen 104 by means of the seal 120 to minimize the throughput of heat or moisture.

FIG. 13 reflects how the robotic arm 160 moves radially, along the double ended arrow F. In essence, the robotic arm 160 is located on a sled 124 and moves along the direction of the double ended arrow F. The sled 124 is provided on one outboard edge with gearing 126 which coacts with a gear G23 driven by a motor M3 having an output shaft provided with another gear G13 shown in FIG. 13. Thus, driving gear G23 causes the sled 124 to move along the direction of the arrow F. Since the robotic arm is carried on the sled 124, it moves within the slit 122.

In addition, the sled 124 supports another motor thereon, the motor M4 provided with a drive means such as a chain 128 driven by gear G14 of the motor which coacts with a complementally formed sprocket 132. The sprocket 132 is fixed to the robotic arm 160. FIG. 14 shows the sled 124 moved so that the robotic arm 160 is near the center of the device.

Figure 15:
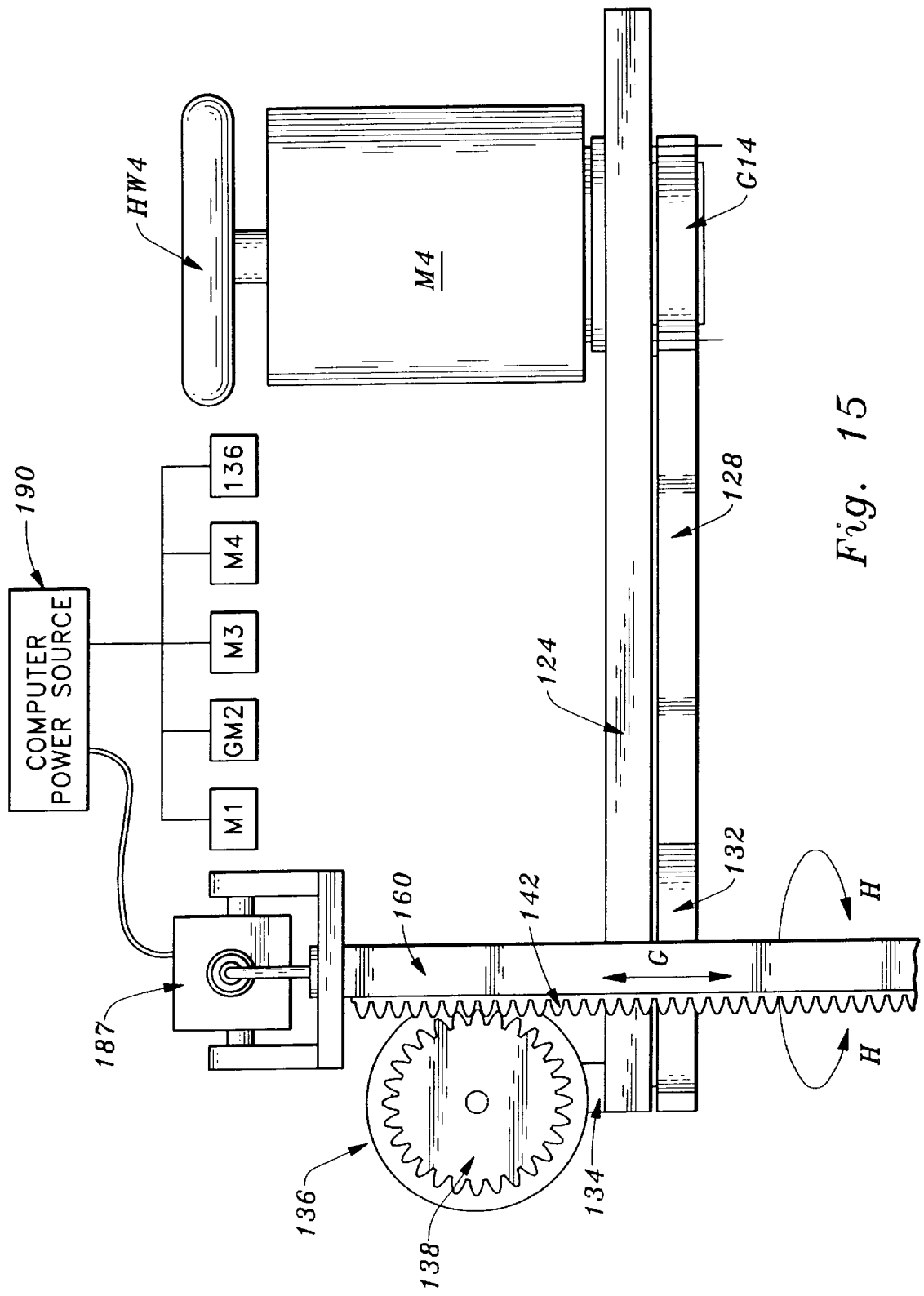
FIG. 15 is a side view of a portion of the top.

With respect to FIG. 15, rotation of the chain 128 by motor M4 through gear G14 causes the robotic arm 160 to move. Preferably, the degree of rotation about the direction of the double ended arrow H is 180°. It will be observed (FIG. 1) that rotation of the robotic arm 180° will allow the robotic arm 160 access to racks on opposite sides of each annular passageway 30. Further, with respect to FIG. 15, it is to be noted that the sprocket 132 includes an upwardly extending projection 134. This projection supports a motor 136. In turn, motor 136 is equipped with a gear 138 adapted to mesh with the pinion 142 integrally formed on the robotic arm 160. Thus, as the sprocket 132 rotates about the direction of the double ended arrow H, the motor 136 is always in threaded engagement with the pinion 142 to allow advancement of the robotic arm vertically, i.e. along the direction of the double ended arrow G.

The motion just described is also shown from another vantage point in FIG. 16. Recall that the elevator 75 is shown with different types of elevator drives. One drive (GM2) mentioned hereinabove could also be the drive shown in FIG. 16. Hand wheels e.g. HW3, HW4, similar to HW1 and HW2 can be attached to the a motors for manual override.

Figure 17:
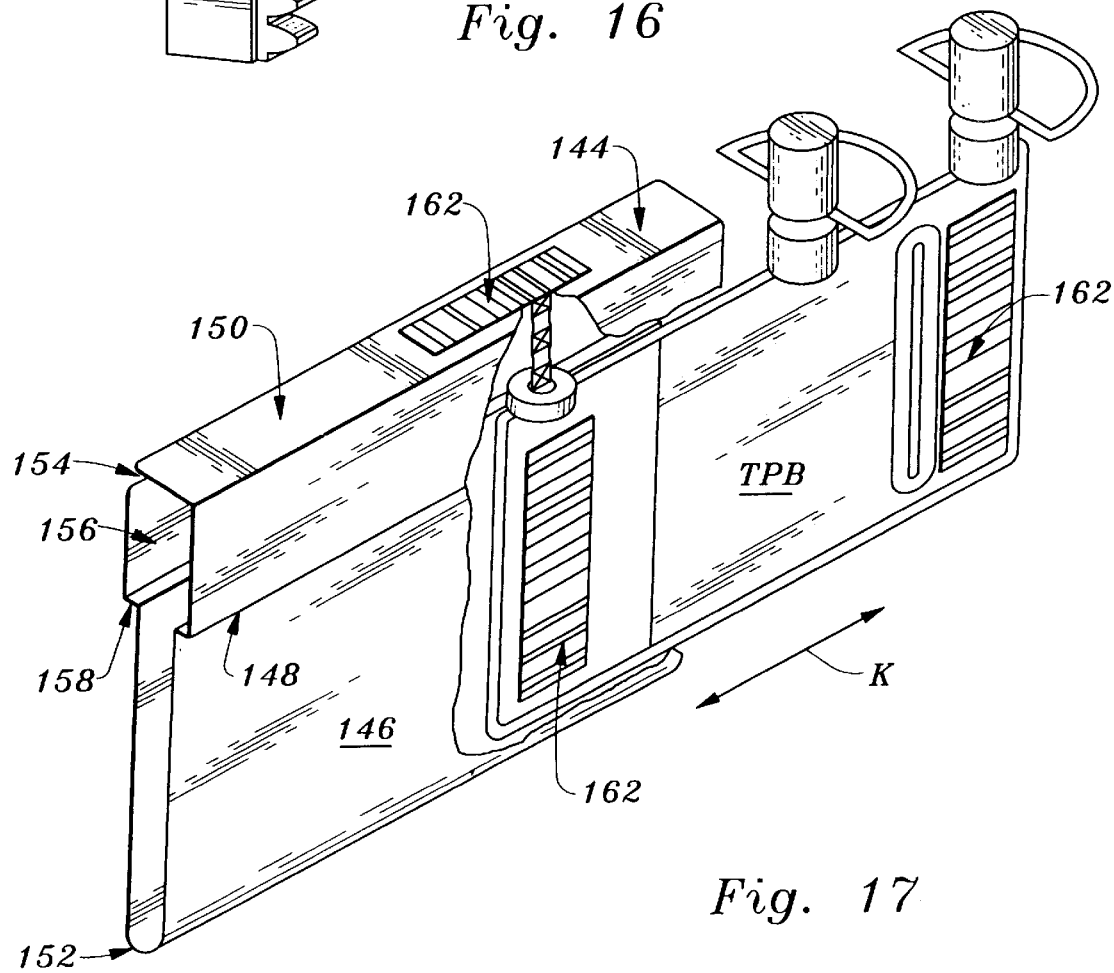
FIG. 17 is a perspective view of the holder and product.

Details of the holder 150 can now be explored. Viewing FIG. 17, the holder 150 is preferably a black body radiator formed from spring metal material, having open end walls which allow the slideable insertion therewithin of a thermolabile product bag TPB. More particularly, the holder 150 includes a top wall 144 having longitudinal edges and latitudinal edges. One longitudinal edge supports a downwardly depending first side wall 146. The side wall 146 includes an upper portion and a lower portion, where the line of demarcation between the lower and upper portions is defined by an inwardly directed ridge 148. The ridge 148 causes the lower portion to be necked-down somewhat concluding in a bottom wall 152 which forms a hairpin turn. The bottom wall 152 communicates with an upwardly extending second side wall 156 having similarly formed upper portions and lower portions and an analogous ridge 158. However, the second side wall 156 includes a free end 154 proximate to the second longitudinal edge of the top wall 144. Since this holder 150 is formed from spring like material, it is programmed with sufficient resiliency and memory to maintain the shape shown in FIG. 17, but allows deformation to allow slideable insertion therein of the thermolabile product bag TPB shown in FIG. 17, when the bag is advanced in the direction of the arrow K. A further characteristic of the top wall 144 is that, similarly to the bag TPB, it may include a form of locating means 162 depicted in FIG. 17 as a bar code.

Figure 19:
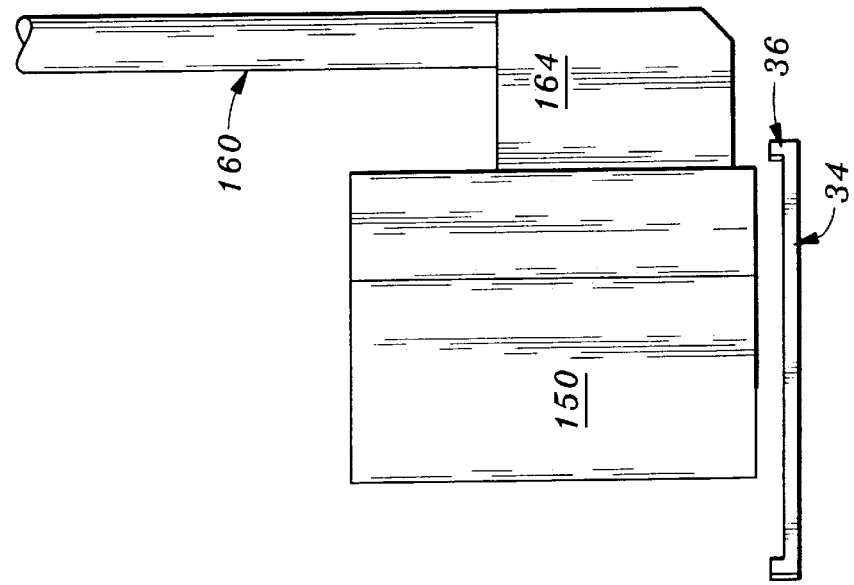
FIG. 19 is a perspective view of the robotic arm and head grasping a holder.
Figure 18:
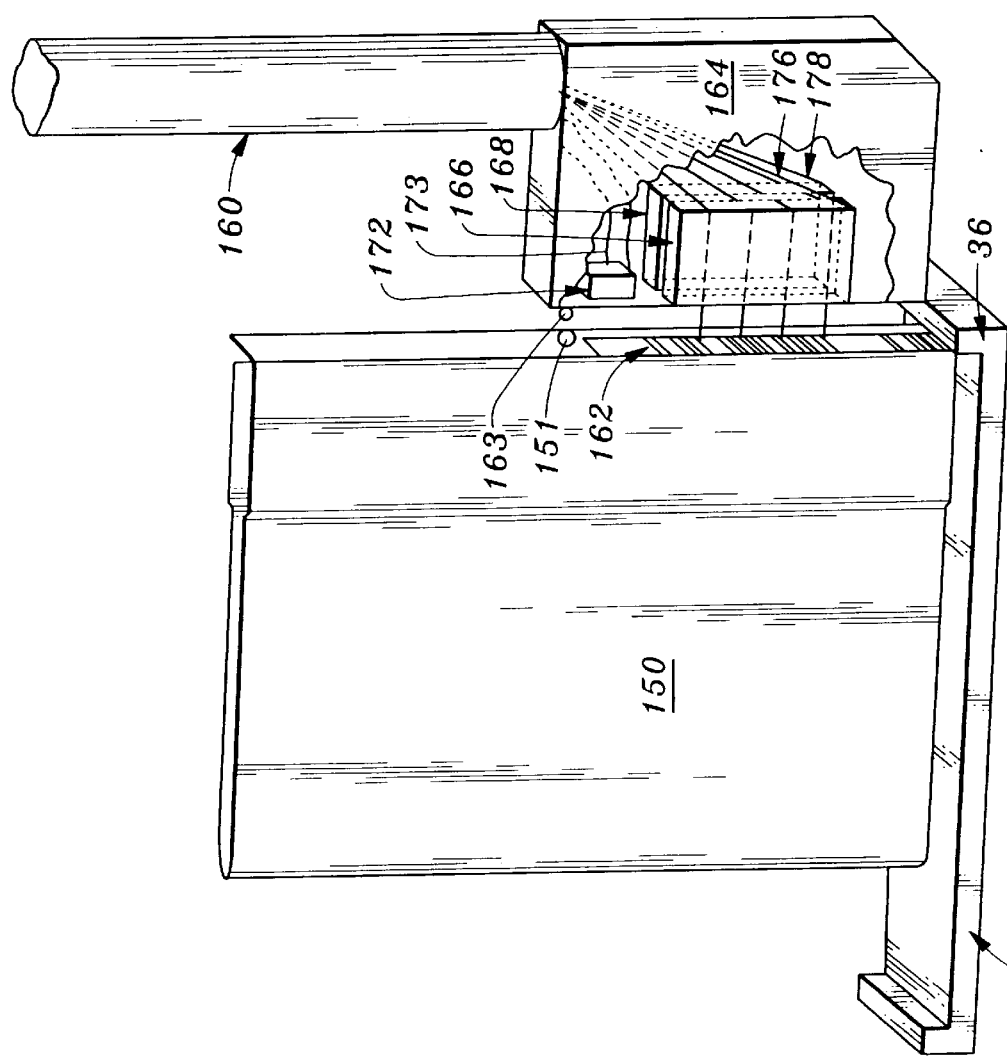
FIG. 18 is a perspective view of the robotic arm and head accessing a holder.

Details of the robotic arm 160 can now be best appreciated since it is adapted to coact with the holder 150. As shown in FIGS. 18 and 19, the robotic arm 160 includes, at its lowermost portion, a head 164. Recall the arm, when rotated about the double ended arrow H of FIG. 15, can address holders 150 on either side of an annular passageway 30 with respect to the support rack 40. The head 164 of the robotic arm 160 includes means for transmitting a signal, the transmitter 166 illustrated as an optical fiber bundle. In addition, means for receiving a reflected optical signal is provided, the receiver 168 configured also as an optical fiber bundle. When the head 164 is to access one of the holders 150 contained within the storage rack 40, it goes to the known location where the product of interest is purported to be stored. The transmitter 166 and receiver 168 confirm that the correct site has been located. Thereupon, and with respect to FIGS. 18 and 19, the head 164 latches onto the holder 150 by energization of a means for collecting the holder 150. In one form of the invention, the holder 150 is connected to the head 164 of the robotic arm 160 by means of a magnetic coupler 172 electrically energized. As shown in FIG. 19, once the holder 150 and head 164 have been placed in tangential registry, the magnetic coupler 172 is energized, locking the two together. The holder 150 then is raised slightly to clear the ledge 36 contained on the shelf 34, discussed earlier. The head 164 of the robotic arm 160 can then proceed to the elevator. FIG. 9 shows the head 164 accessing the elevator in its lowermost position for pick-up or return of a holder 150 having a product. As shown in FIGS. 15 and 18, the transmitter 166 communicates with a computer and power source 190 depicted graphically in FIG. 15. To this end, a fiber optic bundle 176 extends between the transmitter 166 and a light camera assembly 187 interposed between an end of arm 160 and the computer-power source 190; a receiver fiber optic bundle 178 similarly extends between the receiver 168 and the computer-power source 190 through the camera 187; and a magnet conductor 173 extends between the magnet coupler 172 and the computer-power source 190. Essentially, the computer-power source 190 regulates all of the motors associated with the robotic arm 160 and optionally with the elevator 75. In this way, the conduct of the robotic arm 160 can be precisely controlled to assure that the exact product is stored in an exact location and is retrievable as is desired.

Moreover, it may be beneficial for the orientation for the rack 40 within the container 20 to include an absolute reference point RP for initialization of the robotic arm with respect to the computer and all the storage addresses or compartments 32 located within the device 10. In this way, the system can always be reinitialized even if it is required that the system revert to standby power, for example, during a power failure. An example of a reference point RP could be near one elevator 75 shown in FIG. 9. Also, FIG. 9 shows the provision of a duplicate transmitter 166 and receiver 168 for added safety should the components of head 164 need verification.

FIG. 3 shows that there are a multiplicity of access portals 80. It is intended that of the multiple portals, one (80r) be reserved for retrieval and the remainder (80i) be reserved for insertion of the products. In a preferred form of the invention, the retrieval access portal can be specialized in that the holder 150 reside within a dewar 87 so that liquid nitrogen can be added and ensconce the holder 150 and product by means of a spigot 88 in fluid communication with a top open area of the dewar 87. In this way, the product contained within the holder 150 is maintained at an extremely cold, temperature without any adverse temperature spikes. Conversely, the insertion access portals are contemplated as including heating means in the form of halide bulbs 85 so that the rate at which the product freezes can be controlled. The bulbs, at least one each side of the holder 150, benefit from a parabolic reflector 91 focusing and collimating the radiant energy.

Figure 20B:
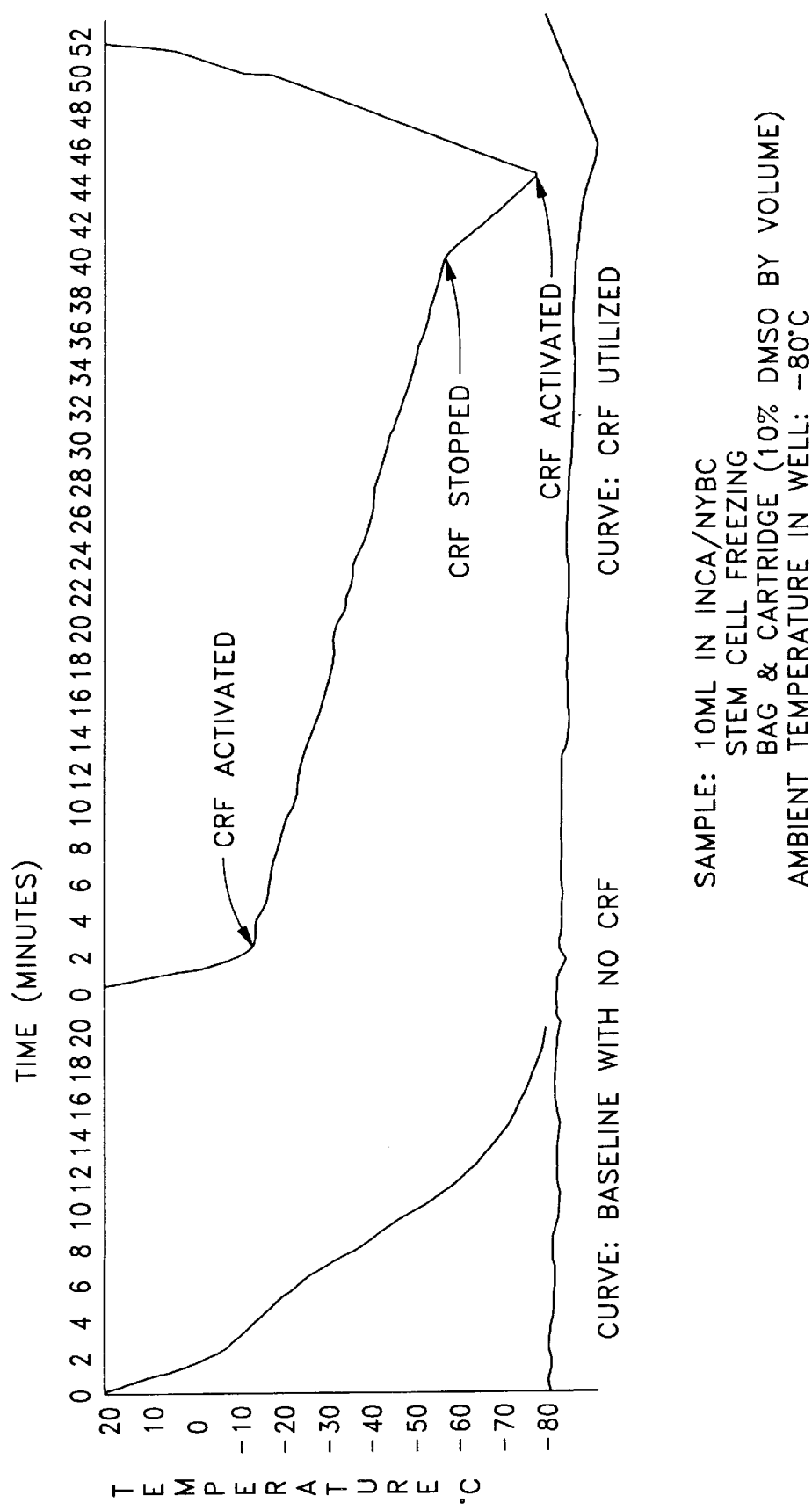
FIG. 20B is another algorithm showing the benefit of controlled rate freezing as a function of temperature.

FIGS. 20A and 20B illustrate controlled rate curves and algorithms which optimizes the manner in which the product is to be frozen. It is believed that each product may have a preferred rate at which the freezing process is to take place. One attribute of the black body configuration of the holder 150 is that it reacts extremely quickly to the ambient conditions within the device 10. The purpose of the halide bulbs 85 can be to slow the rate at which freezing occurs, functioning as a heat gate, to optimize the quality of the product. In addition, a feedback loop, supplementing the algorithm can enhance the system. Further, the holder 150 may include a recess 151 which can receive a probe 163 to monitor the temperature profile.

It is also preferred that storage space be maximized. Thus, the liquid (especially liquid nitrogen) extends to the topmost portion of the storage racks 40. Thus, a gas cap extends above the storage racks and is the temperature that a holder 150 sees when it initially is placed within the device 10. Typically, the liquid nitrogen resides at −190° C. whereas the gas cap of gasified nitrogen resides at −150° C. In certain instances, and because the black body radiator of the holder 150 is so efficient in providing heat transfer, it is desirable to retard the rate at which the product is allowed to descend in temperature. Thus, the halide bulbs 85 control the rate at which the freezing occurs. As mentioned hereinabove, the holder 150 is formed from spring material. Typically the product is contained within a bag having a minimal thickness. When the product is passed beyond one open end wall of the holder 150, the force of the spring of the holder 150 causes the product to assume minimal thickness. This also assures rapid cooling.

In use and operation, the thermolabile product is typically contained within a bag that has plural indicator means 162 which matches to the source product type, and the indicator means 162 contained on the holder. A bar code is illustrated. This data is loaded into the computer for initialization. Next, the thermolabile product within the bag is placed within the holder 150. Next, the product and holder 150 address the access portal 80. Assume that the computer has received sufficient input such that it knows what the preferred algorithm is (see e.g. FIGS. 20A and 20B for illustrations of preferred freezing profiles) and this information is contained within a library of profiles stored in the computer 190. Thus, the halide bulb 85 controls the protocol for having the holder and product descend in temperature once the product has been loaded and lowered as shown in FIG. 9. The left side of each FIG. 20 reflects the freezing profile without thermal intervention, as a function of device temperature. The right-hand side of these figures denote the beneficial results of controlled rate freezing, primarily by slowing down the process. Thereafter, the head 164 of the robotic arm 160 deliver the product to the appropriate location and stores holder 150 and product in rack 40. After the product is stored in its appropriate location, the robotic arm can park, be reinitialized or reused.

In order to effect retrieval of a holder 150 and product, the operator accesses the controlling computer 190 and identifies which product is to be retrieved. The robotic arm 160 locates the product in the holder 150, scans the indicator means 162 (e.g. bar code 162), magnetically docks with the holder 150 after confirmation of the bar code and then removes the holder 150 and product from the storage location where it accesses an elevator 75 which has been lowered to receive the holder and product. The product and holder are placed within a removable vessel, such as a dewar 87 in one of the access portal elevators. The dewar 87 is filled with liquid nitrogen which has been filled by means of a spigot 88 located on a side wall of the container. Once the dewar 87 has been filled with liquid nitrogen, the elevator 75 is raised. The redundant transmitter 166 and receiver 168 can verify the bar code. Lastly, the access portal 80 is opened and the product is made available for subsequent use.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A method for storing and retrieving thermolabile products, the steps including:
    orienting the thermolabile product adjacent the container,
    placing the thermolabile product in the container,
    grasping the thermolabile product with a free end of a robotic arm and
    decreasing the temperature of the thermolabile product at a controlled rate, and
    storing the thermolabile product in a specified site by moving the free end of the robotic arm to the site and releasing the product.

2. The method of claim 1 including:
    subsequently retrieving the thermolabile product by recalling the site of the thermolabile product, directing the robotic arm to the thermolabile product located at said site, verifying that the desired thermolabile product has been located, attaching the robotic arm to the thermolabile product, and delivering the thermolabile product to an exterior of the container.

3. The method of claim 2 further including using a computer for storing profile data with respect to the thermolabile product,
    storing in the computer an indicator number unique to the product,
    placing the indicator number on the product,
    placing the indicator number on an associated holder to be used in storing and retriving the thermolabile product, and
    providing a reader associated with the robotic arm for reading the indicator on holder.

4. A method for storing and retrieving thermolabile products, the steps including:
    orienting the thermolabile product adjacent the container,
    placing the thermolabile product in the container,
    grasping the thermolabile product with a robotic arm,
    decreasing the temperature of the thermolabile product at a controlled rate,
    storing the thermolabile product in a specified site,
    subsequently retrieving the thermolabile product by recalling the site of the thermolabile product, directing the robotic arm to the thermolabile product located at said site, verifying that the desired thermolabile product has been located, attaching the robotic arm to the thermolabile product, and delivering the thermolabile product to the exterior of the container,
    using a computer for storing profile data with respect to the thermolabile product,
    storing in the computer an indicator number unique to the product,
    placing the indicator number on the product,
    placing the indicator number on an associated holder to be used in storing and retrieving the thermolabile product, and
    providing a reader associated with the robotic arm for reading the indicator on the holder.

5. The method of claim 4 further including decresing the temperature at a controlled rate by resting temperature drop via heating.

6. The method of claim 5 further including forming the holder as a thermally conductive black box radiator and enveloping the product first in a product bag and then in the holder.

7. The method of claim 6 further including dimensioning the holder by size and material to squeeze the product bag conforming the product bag to substantially uniform cross-section.

8. The method of claim 7 including retrieving the holder and product by placing the holder and product in a dewar and filling the dewar with liquid nitrogen.

9. The method of claim 8 including parking the robotic arm above a liquid level in the container.

10. The method of claim 9 including locating all drive mechanisms above the liquid level.

11. The method of claim 10 including locating the robotic arm on a lid of the container and moving the robotic arm vertically in and out of the container,
    rotating the robotic arm about its long axis,
    and rotating the lid about a center of the lid.

12. A method for storing and retrieving thermolabile products, the steps including:
    orienting the thermolabile product adjacent the container,
    placing the thermolabile product in the container,
    grasping the thermolabile product with a robotic arm,
    decreasing the temperature of the thermolabile product at a controlled rate,
    storing the thermolabile product in a specified site,
    using a computer for storing profile data with respect to the thermolabile product,
    storing in the computer an indicator number unique to the product,
    placing the indicator number on the product, placing the indicator number on an associated holder to be used in storing and retrieving the thermolabile product, and providing a reader associated with the robotic arm for reading the indicator on the holder.

13. A method for storing and retrieving thermolabile products, the steps including:

orienting the thermolabile product adjacent the container, holding liquid nitrogen in the container;

placing the thermolabile product in the container, grasping the thermolabile product with a robotic arm, decreasing the temperature of the thermolabile product at a controlled rate, and storing the thermolabile product in a specified site by lowering the product into the liquid nitrogen with the robotic arm.

14. The method of claim 13 further including the step of:

storing the thermolabile product while immersing the product in liquid nitrogen using only a free end of the robotic arm and retaining robotic arm drive elements above the liquid nitrogen.

15. The method of claim 13 further including the steps of:

grasping the thermolabile product with a free end of a robotic arm, and storing the thermolabile product in a specified site by moving the free end of the robotic arm to the site and releasing the product.

* * * * *